(12) United States Patent
Sel et al.

(10) Patent No.: US 8,206,442 B2
(45) Date of Patent: Jun. 26, 2012

(54) INTRAOCULAR LENS DEVICE FOR THE IMPROVEMENT OF VISION IN CASE OF RETINAL DISEASES

(75) Inventors: Saadettin Sel, Halle (DE); Jörg Heber, London (GB)

(73) Assignee: Philipps-Universität Marburg, Marburg (DE)

( * ) Notice: Subject to any disclaimer, the term of this patent is extended or adjusted under 35 U.S.C. 154(b) by 34 days.

(21) Appl. No.: 10/576,326

(22) PCT Filed: Oct. 19, 2004

(86) PCT No.: PCT/DE2004/002328
§ 371 (c)(1),
(2), (4) Date: Jan. 24, 2007

(87) PCT Pub. No.: WO2005/039451
PCT Pub. Date: May 6, 2005

(65) Prior Publication Data
US 2007/0198083 A1    Aug. 23, 2007

(30) Foreign Application Priority Data
Oct. 20, 2003   (DE) .................................. 103 49 254

(51) Int. Cl.
*A61F 2/16*   (2006.01)
(52) U.S. Cl. ....................... 623/6.26; 623/6.13; 623/6.25
(58) Field of Classification Search ................ 623/6.13, 623/6.22, 6.25, 6.26, 4.1, 6.11, 6.19, 6.23, 623/6.27–6.32, 6.38–6.4, 6.43, 6.62, 6.17, 623/6.24, 6.3, 6.31, 6.6; 600/398
See application file for complete search history.

(56) References Cited

U.S. PATENT DOCUMENTS

| | | | | |
|---|---|---|---|---|
| 4,581,031 A * | 4/1986 | Koziol et al. | ................. | 623/6.26 |
| 4,601,545 A * | 7/1986 | Kern | ............................. | 349/200 |
| 4,673,406 A * | 6/1987 | Schlegel | ...................... | 623/6.25 |
| 4,731,079 A * | 3/1988 | Stoy | ................ | 623/6.58 |
| 4,828,558 A * | 5/1989 | Kelman | ...................... | 623/6.13 |
| 4,881,805 A * | 11/1989 | Cohen | .......................... | 351/161 |
| 4,963,160 A * | 10/1990 | Hung et al. | ...................... | 8/507 |
| 5,089,023 A * | 2/1992 | Swanson | ..................... | 623/6.25 |
| 5,203,788 A * | 4/1993 | Wiley | .......................... | 623/6.22 |
| 5,481,302 A * | 1/1996 | Yamamoto et al. | ........ | 348/223.1 |
| 5,489,302 A * | 2/1996 | Skottun | ....................... | 623/6.13 |
| 5,712,721 A * | 1/1998 | Large | ............................ | 359/245 |
| 5,728,156 A * | 3/1998 | Gupta et al. | .................. | 623/6.26 |
| 6,244,707 B1 * | 6/2001 | Faubl | ....................... | 351/160 H |
| 6,786,928 B2 * | 9/2004 | Callahan et al. | ............. | 623/6.18 |
| 6,835,204 B1 * | 12/2004 | Stork et al. | .................. | 623/6.25 |

(Continued)

FOREIGN PATENT DOCUMENTS
DE        3439551        4/1986
(Continued)

*Primary Examiner* — Paul Prebilic
*Assistant Examiner* — Leslie Coburn
(74) *Attorney, Agent, or Firm* — Clark & Brody

(57) ABSTRACT

The invention concerns an intraocular lens device which is used in particular for treatment of diseases of the central retina (macula) with retinal areas which are still healthy.

The main principle of the invention at hand is that a lens device is provided for the redirection of the focal point from an area with impaired retinal function to a functioning area which comprises at least one convex lens element and several wedge-shaped recesses.

Surprisingly it was found that a considerable reduction of the thickness of the lens device is thus achievable when several wedge-shaped recesses are provided.

18 Claims, 6 Drawing Sheets

U.S. PATENT DOCUMENTS

| | | | |
|---|---|---|---|
| 7,410,500 B2 * | 8/2008 | Claoue | 623/6.26 |
| 2003/0014107 A1 * | 1/2003 | Reynard | 623/6.24 |

FOREIGN PATENT DOCUMENTS

| | | |
|---|---|---|
| DE | 19751503 | 5/1999 |
| EP | 0 212 616 | 3/1987 |
| EP | 0897293 | 2/1999 |
| EP | 1 475 055 | 11/2004 |
| JP | 61-159964 | 7/1986 |
| JP | 62-079054 | 4/1987 |
| WO | WO98/05272 | 2/1998 |
| WO | 03/047466 | 6/2003 |
| WO | 2005/011531 | 2/2005 |

* cited by examiner

INTRAOCULAR LENS DEVICE FOR THE IMPROVEMENT OF VISION IN CASE OF RETINAL DISEASES

STATE OF THE ART

The invention concerns an intraocular lens device which serves for the improvement of vision in the case of retinal and macular diseases in particular.

Frequent causes of visual impairment in humans are pathological changes of the ocular fundus (the retina, choroid and sclera). These changes can lead to the degradation of retinal function. The task of the retina is the neurosensory processing and transmission of the incoming light stimuli. Vision is impaired to impossible with areas of the retina pathologically changed, possibly leading to losses of the field of vision at these sites.

The normal eye focuses with the help of the refraction media (cornea and lens) the incoming light in the macula. The macula is a retinal area with the highest optic resolution at the posterior pole of the eye. Pathological changes of the macula can lead to a considerable degradation of vision. Affected persons can not perform normal activities such as reading or driving, since the light rays are projected by the natural, biological lens onto the pathologically changed macula. It is thus impossible for patients to recognize a fixed object. In most cases of illness, the entire retina or macula is not damaged, but still features healthy areas. Therefore, vision could be improved considerably by refraction of the light rays onto these healthy retinal areas with the help of an intraocular lens device.

So far, several intraocular lens devices are known which are intended for the improvement of vision in macular diseases.

The U.S. Pat. No. 4,581,031 describes an intraocular lens device for the improvement of vision in patients with loss of the central field of vision. This concerns a lens device which redirects the retinal images to a functioning area of the retina by means of a prismatic portion. In patent EP 0897293 B1, this invention was improved, whereby a pair of intraocular lenses are used enabling the vision of targets at different distances. A prismatic portion which is composed of a material with a high refraction index in the range of 1.5-1.6 was likewise used for the redirection of the focal point on the retina.

The published patent application DE 19751503 A1 describes a prismatic intraocular lens with an integrated concentric prisma which can be used as a replacement for the human lens in the eye for the improvement of vision after cataract surgery in patients with diseases of the central retina (e.g. the macula). Since the devices are introduced into the eye, it must be ensured that they do not slip. According to the present state of the art, this is achieved by means of stabilizing parts (haptics). Other fixation devices which prevent slipping can also be used.

The aforementioned devices from the present state of the art feature the following disadvantages:

1. The devices from U.S. Pat. No. 4,581,031, DE 19751503 A1 and EP 0897293 B1 must be designed voluminously as well as rigidly and therefore heavily in order to cause an optic corrective effect in the form of a redirection of the focal point. Furthermore, materials with a relatively high refraction index (according to the present state of the art between 1.5 and 1.6) must be used for sufficient redirection of the focal point.

2. Vision is only restored by a very marginal amount by defocusing (DE 19751503 A1). The circular focal zone leads solely to elucidation of the field of vision.

Thus these devices are only able to be used by a small number of patients and only lead to moderate optic improvements with a very poor wearing comfort for these patients.

AIM OF THE INVENTION

Hence, the aim of the current invention is to produce a lens device which is characterized by a smaller size and improves the vision of the affected person to a maximum, whereby the lens device should be as adjustable to the respective disease pattern as possible.

Through the desired size reduction, surgery-caused complications can be considerably reduced and patients' convalescence can be shortened, as the surgeon needs a shorter cut in order to introduce the lens into the eye. Due in particular to the foldability of the intraocular lenses, the cutting length can be shortened even more.

Based on the current invention, the given aim is achieved by a lens device according to patent claim 1. FIG. 1 shows the developed device in a first practical embodiment.

In order to achieve this aim, two influential factors with opposite effects have to be taken into consideration.

On the one hand, the thickness of the device has to be minimized in order to be adjustable to the geometry of the eye, and on the other, it must be characterized by a determined thickness in order to move an image to a healthy area of the retina.

The main principle of the current invention is based on the redirection of the focal point—which is generated by one or several convex parts of the lens device—from the area with impaired retinal function to an area capable of functioning, through wedge-shaped recesses in the lens device, whereby the wedge-shaped recesses are characterized by inclined areas which cause the redirection of one or several focal points.

The inclination angle of the inclined areas does not have to be identical for all inclined areas of the recesses.

Surprisingly, it has been discovered that a significant reduction of the thickness of the lens device can be achieved by providing several wedge-shaped recesses, for instance, on the reverse side, i.e. on the side directed towards the retina, for instance in the form of a Fresnel prism, whereby a sufficient redirection of the focal point remains adjustable.

The table shown below indicates determined refraction indices of possible materials (column 1), the required prism angle (column 2), and subsequently compares the additional thickness added by a lens device according to the technical state of the art to an intraocular lens with the device based on the current invention (columns 3 and 4). The additional thickness, which is caused, for instance, by a Fresnel lens, is N times smaller (N is the number of periods). For example, if N=10, the device based on the current invention will be 10 times thinner. The lens device according to the technical state of the art is plano-convex, typically with a diameter of 6 mm, and has its focal point at the distance a.

| Refraction index $n_1$ of the optical material | prism angle $\epsilon$ for an adjustment by 1.0 mm (in degrees) | Additional thickness for an intraocular lens known from the technical state of the art with a diameter of 6.0 mm for a regular prism (in mm) | Additional thickness of a Fresnel lens with 10 periods (in mm) |
|---|---|---|---|
| 1.45 | 34.0 | 3.4 | 0.34 |
| 1.50 | 25.3 | 2.6 | 0.26 |

-continued

| Refraction index $n_1$ of the optical material | prism angle $\epsilon$ for an adjustment by 1.0 mm (in degrees) | Additional thickness for an intraocular lens known from the technical state of the art with a diameter of 6.0 mm for a regular prism (in mm) | Additional thickness of a Fresnel lens with 10 periods (in mm) |
|---|---|---|---|
| 1.55 | 20.0 | 2.0 | 0.20 |
| 1.60 | 16.4 | 1.7 | 0.17 |

The required prism angle can be calculated by means of the following formula (there are, of course, other formulas and/or approximations as well):

$$\arcsin\left(\frac{d}{a}\right) = \arcsin\left(\frac{n_1}{n_2}\sin\varepsilon\right) - \varepsilon,$$

whereby

ε: prismatic angle (36)
d: distance from the macula (22) to the desired healthy point on the retina (46)
a: distance from the macula (22) to the rear level of the intraocular lens (30)
$n_1$: refraction index of the intraocular lens material
$n_2$: refraction index of the aqueous fluid/vitreous body (typically 1.336).

In the table above, the formula was solved numerically. Further typical parameters utilized were: d=1.0 mm; a=17.0 mm, and $n_2$=1.336.

The thickness of the intraocular lens device is controlled by the selection of certain materials with specific refraction indices, whereby the angle required for a specific image displacement, e.g. regarding the Fresnel prisms or the wedge-shaped recesses, is lower when the refraction index is higher.

Another advantage of the device based on the current invention is that in one embodiment it is made of one piece while the devices according to the technical state of the art are composed of different pieces, which can lead to problems during the implantation and regarding the compatibility of the lens devices alien to the body, since lens devices composed of different pieces usually are not characterized by the foldability desired for the implantation (large surgery wound (sclera tunnel incision) required) and are not as compatible as desired.

The locations for the implantation of the intraocular lens device can be different areas of the eye (anterior chamber, posterior chamber or capsule of the natural lens). Depending on the location of the implantation, the fixation devices must be adjusted accordingly based on the technical state of the art.

PRACTICAL EMBODIMENTS

Practical embodiments are outlined in illustrations 1 to 8 and the further description:

The first chamber, i.e. the front part of the lens device, is constructed with elastic, transparent material so that the curve and, therefore, the focal distance of the convex part is variable.

The second chamber is shaped in such a way that the transparent beam of the wedge-shaped recesses can be rotated in relation to them, whereby the rotation occurs against the preliminary tension of an elastic element. Hereby the inclination of the inclined surfaces of the recesses can be varied. The rotation can occur either through self-propulsion directly within the rotatable element (49) or through adding a transparent fluid (68) into the second chamber in such a way, that the increased inner pressure within the chamber or within an envelope fixed within that chamber, pressure is exerted towards the rotatable beam element of the recesses.

Figure 8:
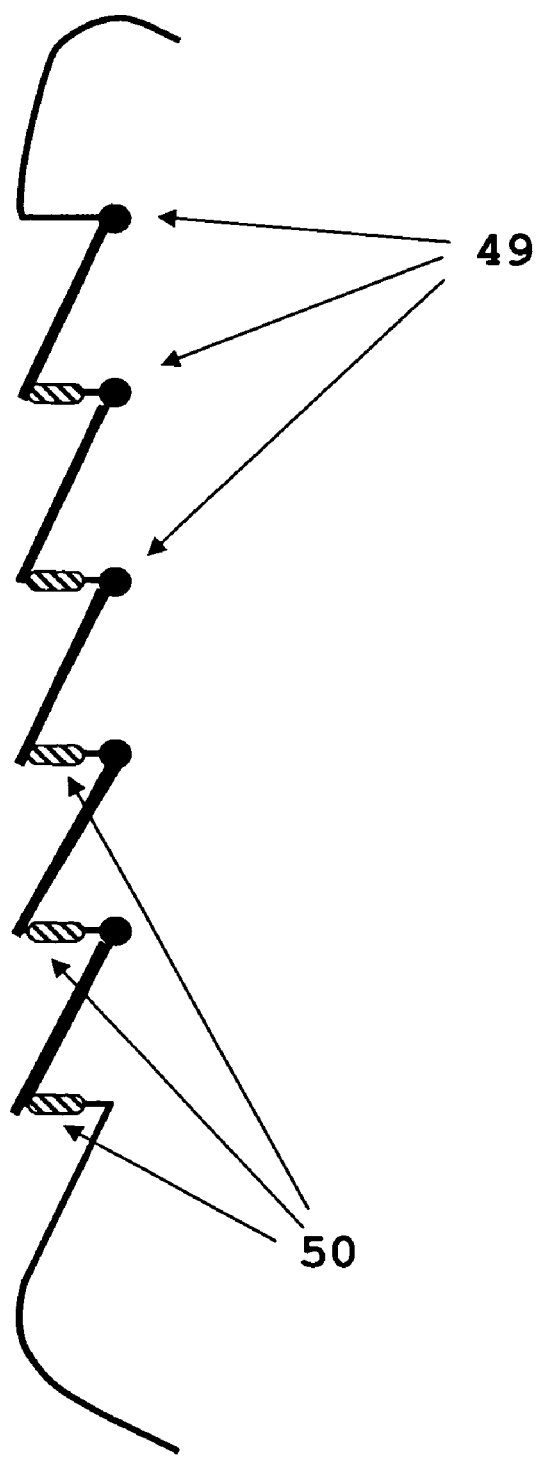

FIG. 8 shows a cut-out of a further advantageous practical embodiment, whereby the wedge-shaped recesses are characterized respectively by one rotatable, transparent and inclined surface. An elastic element which is pre-stressed against the rotation is attached to each of those rotatable inclined surfaces.

Figure 1:
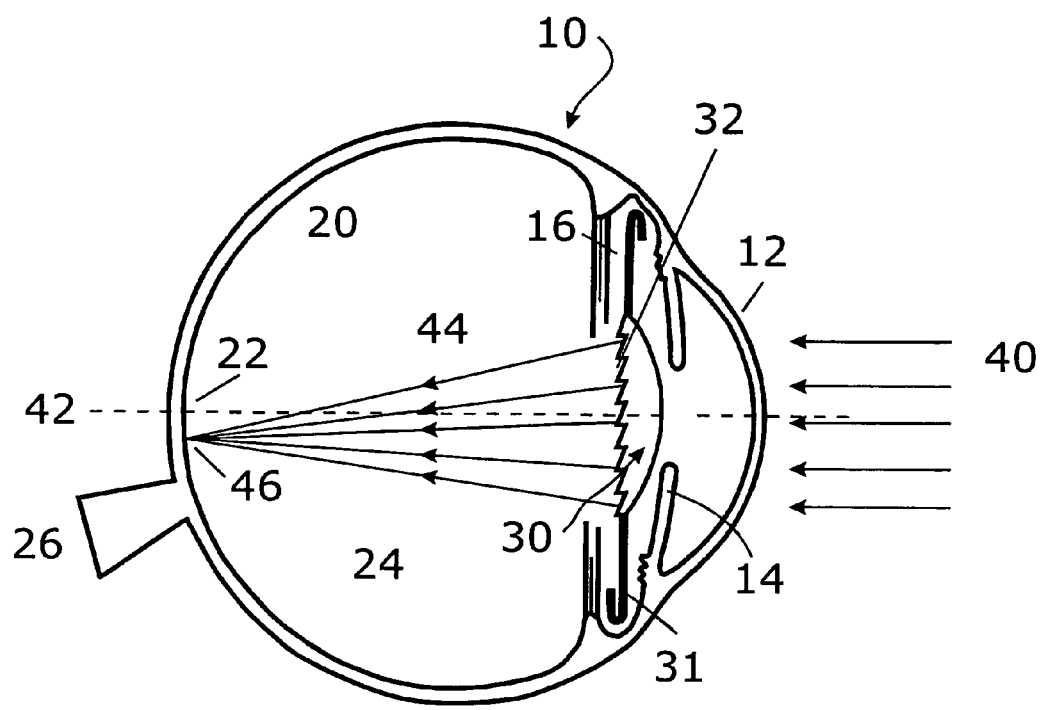
FIG. 1 depicts the human eye in a cross-sectional view with the lens device based on the current invention (30) in the first practical embodiment.

FIG. 1 shows a cross-sectional view of the human eye (10) with the lens device based on the current invention (30). Incoming light (40) parallel to the symmetrical axis (42) of the lens device is bundled by the anterior convex part of the lens device within a focal point and redirected by the wedge-shaped recesses (32) to a new focal point on the healthy retina (20), or respectively, on the macula (22).

Figure 2:
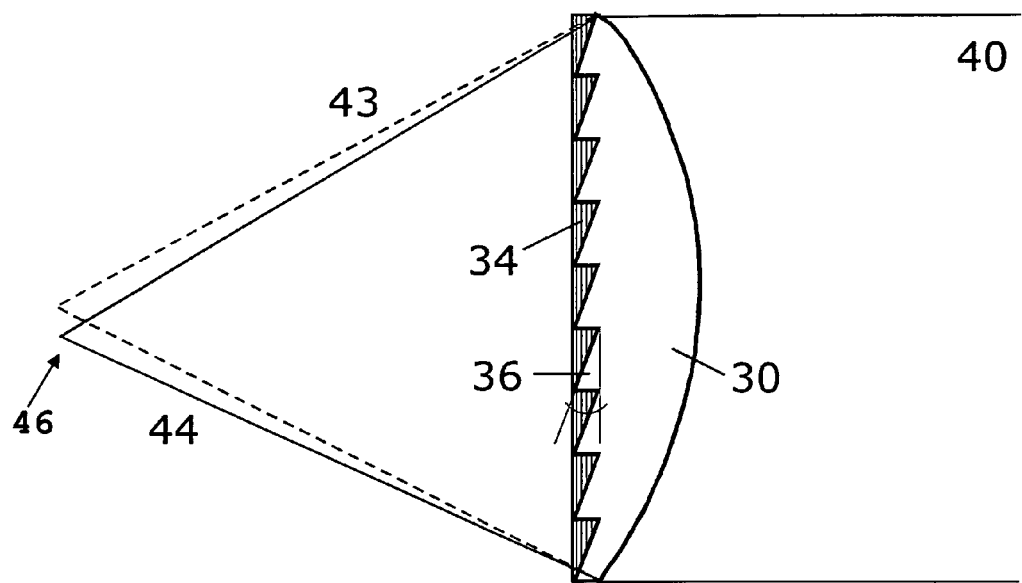
FIG. 2 depicts a detailed view of FIG. 1, including an enfolding protective coating (34).

FIG. 2 shows the device according to FIG. 1, but with a protective coating (34) in order to avoid
a) the depositing of particles or cells within the wedge-shaped recesses (32)
b) reflections at the lens device after having passed through it, and therewith, scattered incidences of light of the lens device to the retina, wherefore the protective coating (34) is equipped with anti-reflection properties.

This also facilitates the post-treatment of cataracts with the help of surgical and/or laser-technical methods. The normal and the modified optical path (43, 44) are clearly visible. In this example all recesses (32) are characterized by inclined surfaces with an identical angle (36). On the surface not facing the retina, a UV protection film or layer (38) is applied, as most recent results of research have shown that the clouding of the lens is not exclusively related to the disease, but also forms a protection of the retina located behind against UV radiation.

Figure 3:
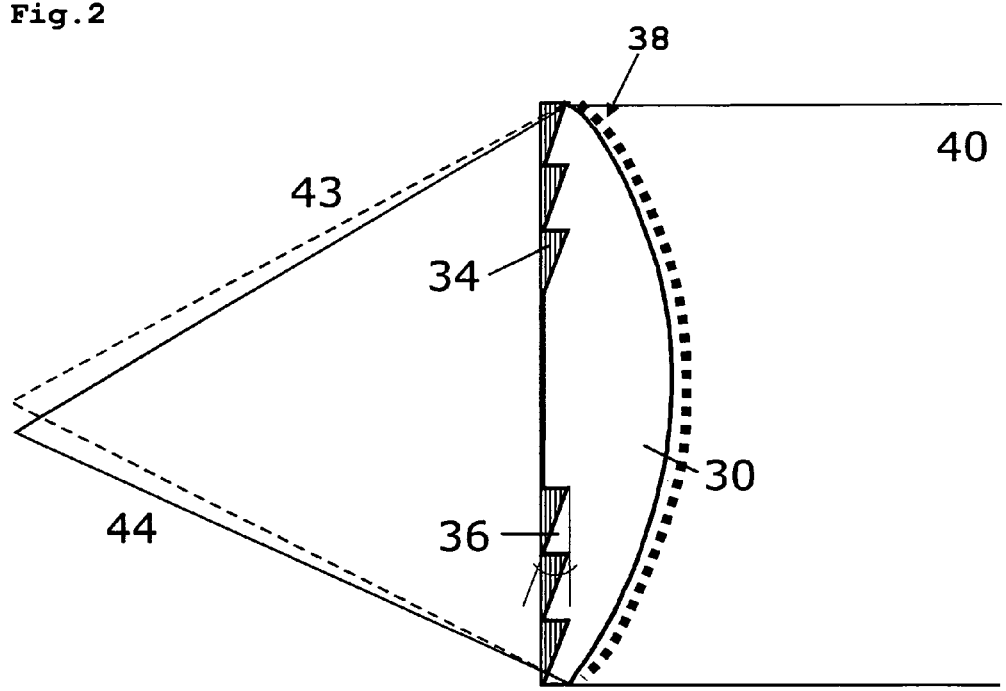
FIG. 3 depicts a practical embodiment with a smooth segment on the side of the device facing the macula (22).

FIG. 3 shows a further practical embodiment, in which in the area of the optical symmetry axis, no recesses (32) are foreseen in order to let the central light rays pass without hindering them.

Figure 4:
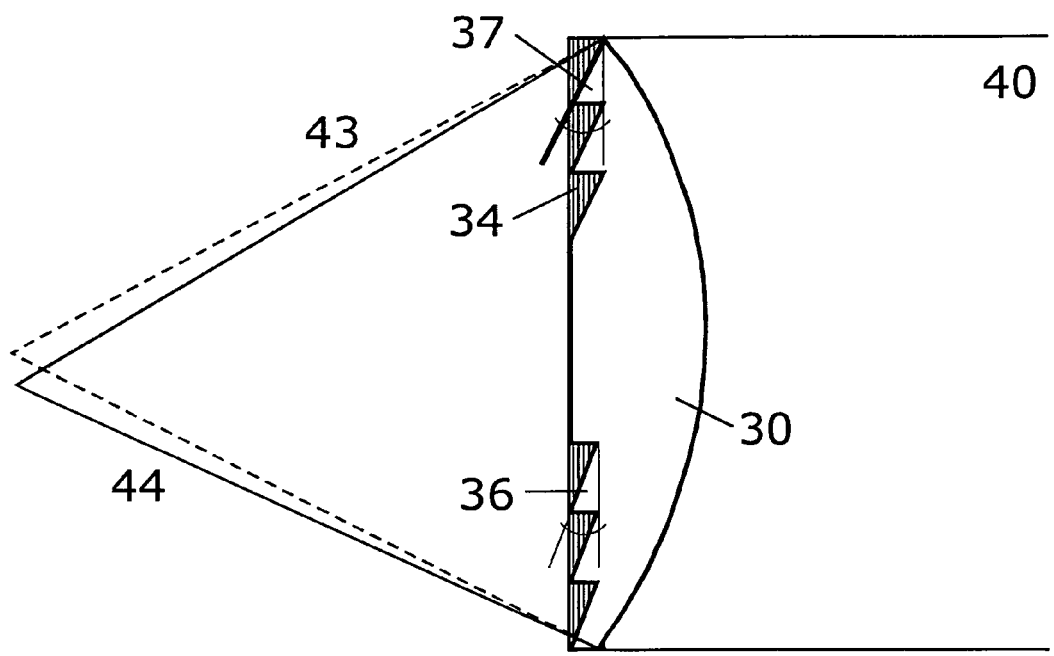
FIG. 4 shows a further practical embodiment with two different inclination angles (36, 37).

FIG. 4 shows the practical embodiment according to FIG. 3, however with different inclination angles (36, 37). Thus different parts of the image can be redirected at varying degrees of strength.

Figure 5:
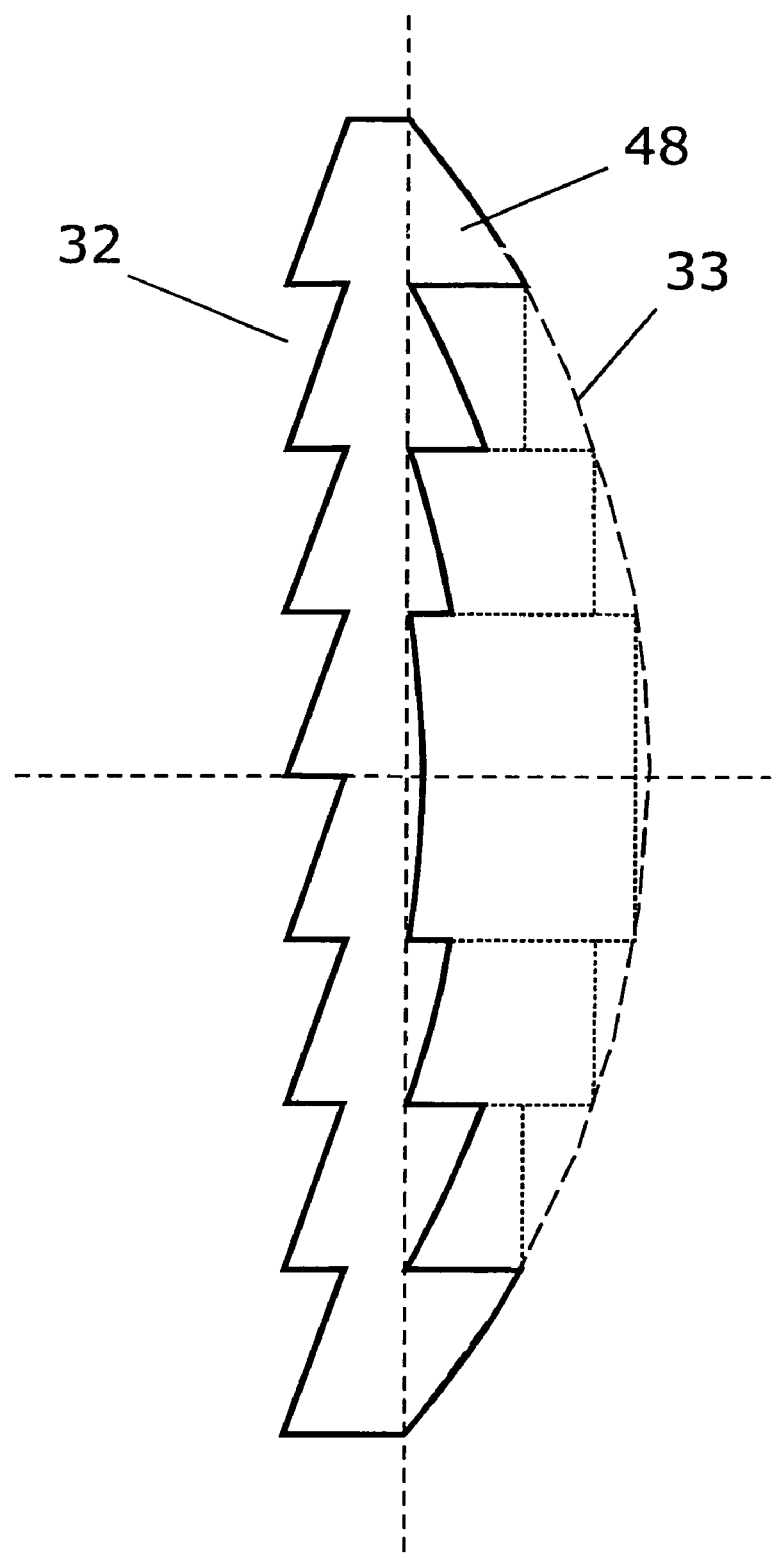
FIG. 5 shows a practical embodiment that is particularly preferred, in which, as the convex part of the lens device, the segments of a Fresnel lens (48) are envisioned in the front part of the lens device and the wedge-shaped recesses are envisioned in the rear part of the lens device which faces the macula. The lens device is depicted by the thick, uninterrupted lines.

FIG. 5 shows a preferred practical embodiment of the lens device (30) based on the current invention in which instead of a one-sided, at least partly convex lens part (33), several concentric convex segments (48) of a Fresnel lens are foreseen and the wedge-shaped recesses are located on the opposite side, facing the macula (22) (the period of the Fresnel lens and the prisms can differ from one another).

Compared with a continuous, one-sided convex lens or parts thereof, the thickness of the lens device can be reduced even more.

A particularly preferred practical embodiment (not illustrated) can be achieved by designing the macular side of the lens device in a planar way and the other side with segments shaped in such a way as when the inclined recesses of the prism device are added to the concentric-convex segments (48) of a Fresnel lens, hereby combining the lens effect and the redirection of the focal point within a Fresnel element. This front side is illustrated in FIG. 5. Thereby the thickness of the lens device can be further reduced. Due to production reasons, it is advantageous in this practical embodiment to reinforce the device, taking the recesses of the combined Fresnel elements out of a sufficiently thick block of material.

Figure 6:
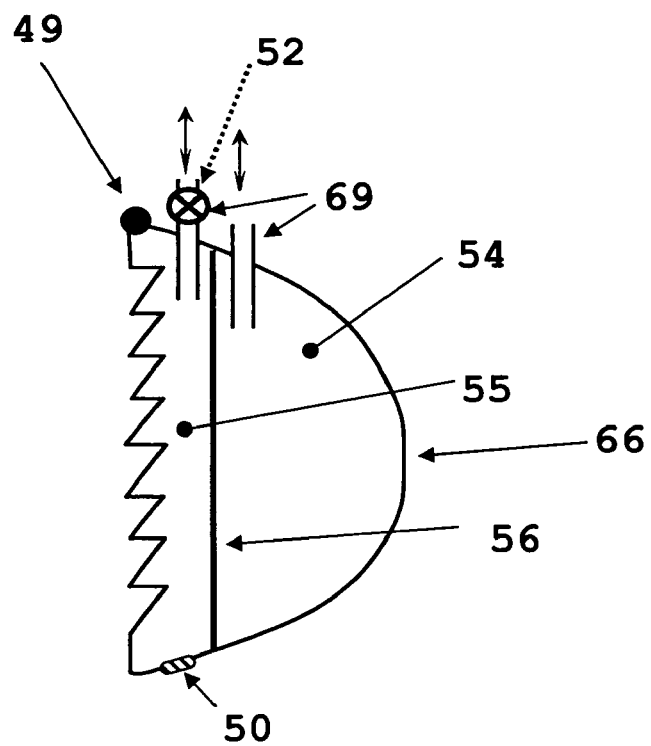
FIGS. 6 and 7 show a further advantageous practical embodiment, in which the lens device has been subdivided into two separate chambers by a wall.

FIG. 6 shows a quite particularly preferred practical embodiment, in which in the front part of the lens device—as part of an anterior chamber (54)—a convex lens element (66) is foreseen, the curve of which can be modified. This lens element can, for instance, if pumping means are envisioned at the lens device, be modified in terms of its curvature by adding or removing via supply and removal canals 69, e.g. chamber fluid or another liquid matching the refraction index of the enveloping material and/or the chamber fluid, or by volume modifying means (51).

Figure 7:
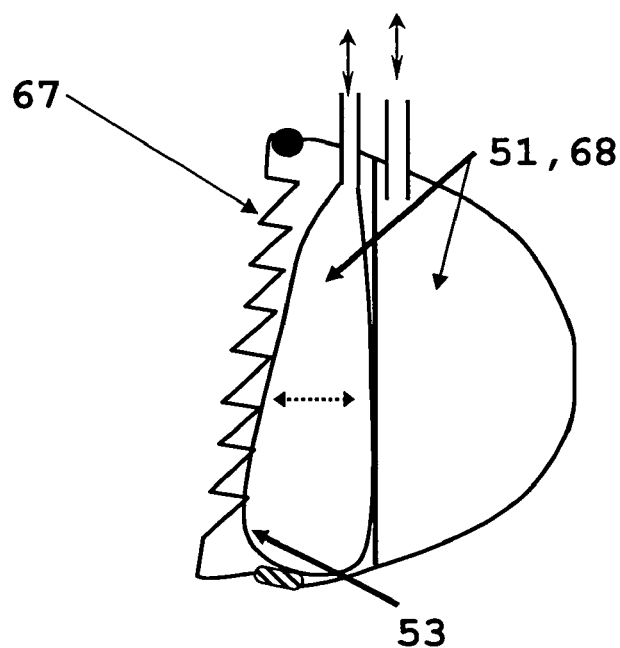

FIG. 7 shows a further quite particularly preferred practical embodiment, characterized by a second posterior chamber (55), separated from the first chamber (54) by a wall (56). In the latter, according to FIG. 7, an elastic and transparent envelope (53) can be foreseen. A part of this second chamber is formed by a transparent supporting element (67) for several wedge-shaped recesses (32), which is fixed in such a way that it can be rotated in the direction of the first, front part of the lens or front chamber around a rotatable element. An elastic element is fixed to the supporting element (67) and pre-stressed against the rotation of the element (67) from the remaining part of the posterior chamber (55). Hereby, it has to be avoided that the perpendicular surface pieces of the wedge-shaped recesses are rotated out of their parallel position towards the optic axis in such a way that they can not take part in the "optical ray path".

By addition or removal of e.g. chamber fluid or a liquid matching the refraction index of the enveloping material and/or the chamber fluid, e.g. through the same or identical pumping means (52) as applied to the first envelope at the front, the rear beam element can be designed in a form allowing, through increasing the volume within an elastic envelope (53) foreseen within the chamber (55), for a modification of its inclination against the optical axis in such a way that the modifiable inclination of the wedge-shaped recesses (32) cause a bigger or smaller redirection of the focal point.

FIG. 8 shows a part of another practical embodiment in which in the second, posterior chamber (55) no elastic envelope is foreseen. To the wedge-shaped recesses respectively one moveable, transparent and inclined surface is assigned, which can be rotated through rotatable elements (49). To each of those moveable inclined surfaces an elastic element (50) is assigned. The rotation of the moveable inclined surfaces is in this case caused due to the fact that through the assigned pumping means, the inner pressure within the posterior chamber (55) is increased. Compared to the practical embodiment of FIG. 7 it is hereby advantageous that the rotation of the—in the unrotated state, horizontal—pieces, which run parallel to the optical axis, does not have to be compensated.

Nano-structured instruments, e.g., which exploit the phenomenon of acoustic surface waves can be utilized as a means of pumping, assisted by adhesion forces if required. Such pumping means are currently (May 2003) available by e.g. the company Advalytix AG in 85649 BRUNNTHAL. It is particularly advantageous to deploy those pumping means, of which the power consumption corresponds to the degree of pressure governing in the inside of the eye. Thus the inner eye pressure could be measured from outside through a measurement of the pumping performance of the pumping means. As an energy source for the volume modification means or pumping means, implanted batteries or receivers and/or converters for the energy input from outside of the patient's body, e.g. through electro- and/or magnetic fields, can be foreseen. As media to modify the volume, apart from the chamber fluid existing within the eye ball, a transparent medium, e.g. also a non-liquid medium, which is adjusted with regard to its refraction index to the refraction index of the chamber wall and/or the elastic envelope (53) can be utilized.

As it is obvious to the person skilled in the art, at locations without wedge-shaped recesses and convex lens portions or segments of a Fresnel lens, but also in combination with those, further optical means, as for instance lenses for the narrow field correction, can be foreseen. Further optical means can of course—due to the gained reduction of the lens device's thickness based on the current invention—be located within the optical path before or behind the lens device based on the current invention. Furthermore the Fresnel lens itself can—thanks to its flexible design—feature zones with different spherical and/or non-spherical curves or segments, in order to obtain additional optical effects, e.g. the realization of a multifocal effect for simultaneous view of narrow and wide.

The invention claimed is:

1. A lens device for the treatment of visual impairments and designed as a segment of a Fresnel lens and wherein a focal point is generated by the lens device comprising:
    an anterior side of the lens and a posterior side of the lens,
    a fixation element for fixing in the eye,
    a plurality of wedge-shaped recesses on the posterior side of the lens, and a superposition of spherical and non-spherical segments of one or more Fresnel lenses on the anterior side of the lens opposite the posterior side,
    wherein the plurality of wedge-shaped recesses include inclined areas, which redirect the focal point through the wedge-shaped recesses, the inclined areas are plane areas running linearly in a parallel direction to each other, the inclined areas and their plane areas running linearly in a parallel direction to each other extend along the entire posterior side of the lens device.

2. The lens device according to claim 1, wherein the wedge-shaped recesses are inclined at different angles.

3. The lens device according to claim 1, wherein the posterior side features a coating or protective layer to fill the wedge-shaped recesses preventing the reflection of light on the edges of the lens device after passage through the lens device.

4. The lens device according to claim 3, wherein the coating features a refraction index equal to that of the chamber fluid of the eye of the patient.

5. The lens device according to claim 1, wherein the lens device features an anterior chamber and a posterior chamber which are separated by a transparent wall, whereby the anterior chamber is configured to face away from the retina and features at least one convex-elastic element, so that by alignment of the curve of the at least one convex-elastic element, the focal width of the at least one convex-elastic element is variable.

6. The lens device according to claim 5, wherein the posterior chamber, which is configured to face the retina, features a transparent, elastic coating, and the posterior chamber features a supporting element for the wedge-shaped recesses, which is designed to be mounted rotatably against the posterior chamber, so that the inclination of the wedge-shaped recesses is adjustable.

7. The lens device according to claim 6, wherein the supporting element is attached to an elastic element which is pre-stressed against rotation.

8. The lens device according to claim 6, wherein each chamber is connected to a supply and removal canal, each of which is assigned at least one pump or volume modification means either directly or indirectly via one or more valves, so that one or more of the convex-elastic element of the anterior chamber and the transparent, elastic coating undergoes a change of form when the pump or volume modification means is activated, and the supporting element for the wedge-shaped recesses undergoes rotation due to the transparent, elastic coating or the convex-elastic element changing its form.

9. The lens device according to claim 8, wherein, in the posterior chamber which faces the retina, a mobile, transparent and inclined surface is assigned to each wedge-shaped recess which is arc adapted to be mounted rotatably due to rotation elements, whereby an elastic element is assigned to each of these mobile, transparent and inclined surfaces and, the mobile, transparent and inclined surfaces undergo a rotation when the pump or volume modification means assigned to the anterior chamber is activated, so that the focal point is redirected on the retina.

10. The lens device according to claim 1, wherein each chamber is adapted to be filled with a transparent medium, whose refraction index is adapted to be adjusted to be that of one or more of the chamber fluid, the transparent, elastic coating, and the transparent wall.

11. The lens device according to claim 8, wherein implanted batteries or receivers are provided as means of providing energy for the at least one pump or volume modification means for inputting energy from outside of a body of a patient.

12. The lens device according to claim 1, wherein optical means for the correction of the near field are provided, whereby the further optical means can also be provided in front of or behind the lens device.

13. The lens device according to claim 1, wherein the lens device features at least one UV-protective film for the protection of the retina from UV rays.

14. The lens device according to claim 8, whereby the pump or volume modification means feature a characteristic curve, which allows conclusions to be drawn on a counter-pressure on a recorded performance of a pump or volume changes, against which the pump or volume modification means work, so that a determination of the pressure in the interior of the eye of the patient is possible via a measurement of the recorded performance.

15. The lens device according to claim 9, wherein each chamber is adapted to be filled with a transparent medium, whose refraction index is adapted to be adjusted to be that of one or more of the chamber fluid: the transparent, elastic coating: and the transparent wall.

16. The lens device according to claim 12, wherein the further optical means is a lens.

17. The lens device according to claim 11, wherein energy input from outside of the body of the patient is by one or more of electromagnetic and magnetic fields.

18. The lens device according to claim 1, wherein a material of the fixation element features a refraction index equal to that of the chamber fluid of the eye of the patient.

* * * * *